US006927406B2

United States Patent
Zyromski

(10) Patent No.: US 6,927,406 B2
(45) Date of Patent: Aug. 9, 2005

(54) MULTIMODAL IMAGING SOURCES

(75) Inventor: Kristiana E. Zyromski, Frazier Park, CA (US)

(73) Assignee: ISO-Science Laboratories, Inc., Valencia, CA (US)

( * ) Notice: Subject to any disclaimer, the term of this patent is extended or adjusted under 35 U.S.C. 154(b) by 47 days.

(21) Appl. No.: 10/278,411

(22) Filed: Oct. 22, 2002

(65) Prior Publication Data

US 2004/0075048 A1 Apr. 22, 2004

(51) Int. Cl.[7] .................................................. G21G 4/00
(52) U.S. Cl. ............................. 250/496.1; 250/252.1; 250/493.1
(58) Field of Search ........................... 250/496.1, 252.1, 250/493.1

(56) References Cited

U.S. PATENT DOCUMENTS

| | | | | |
|---|---|---|---|---|
| 4,613,754 A | * | 9/1986 | Vinegar et al. ........... | 250/252.1 |
| 5,227,627 A | | 7/1993 | Gamarnik et al. | |
| 5,394,457 A | | 2/1995 | Leibinger et al. | |
| 6,072,177 A | * | 6/2000 | McCroskey et al. ..... | 250/252.1 |
| 2001/0004395 A1 | | 6/2001 | McCrory et al. | |
| 2004/0021083 A1 | * | 2/2004 | Nelson et al. | |

FOREIGN PATENT DOCUMENTS

| | | |
|---|---|---|
| WO | WO 00/75691 A1 | 12/2000 |
| WO | WO 03/025621 A1 | 3/2003 |

* cited by examiner

Primary Examiner—Nikita Wells
Assistant Examiner—Zia R. Hashmi
(74) Attorney, Agent, or Firm—Christie, Parker & Hale, LLP

(57) ABSTRACT

A multimodal source for imaging with at least one of a gamma camera, a positron emission tomography (PET) scanner and a single-photon-emission computed tomography (SPECT) scanner, and at least one of a computed tomography (CT) scanner, magnetic resonance imaging (MRI) scanner and optical scanner. The multimodal source has radioactive material permanently incorporated into a matrix of material, at least one of a material that is a target for CT, MRI and optical scanning, and a container which holds the radioactive material and the CT, MRI and/or optical target material. The source can be formed into a variety of different shapes such as points, cylinders, rings, squares, sheets and anthropomorphic shapes. The material that is a target for gamma cameras, PET scanners and SPECT scanners and/or CT, MRI and/or optical scanners can be formed into shapes that mimic biological structures.

25 Claims, 6 Drawing Sheets

MULTIMODAL IMAGING SOURCES

BACKGROUND OF THE INVENTION

The invention is related to medical and molecular imaging of patients and animals with various scanning machines and methods, and more particularly to sealed calibration and reference sources for such scanning machines.

Scientists and physicians have found that in imaging patients and animals, there are advantages in using combinations of two or more of computed tomography (CT) scanning, magnetic resonance imaging (MRI) scanning, gamma camera scanning, positron emission tomography (PET) scanning, single-photon-emission computed tomography (SPECT) scanning, and optical scanning. Recently, scanners that combine CT and PET functionality have gained favor among physicians. However, since these combination machines are costly, many hospitals, physicians and researchers continue to rely on scanning patients and animals consecutively with a CT scanner and then a PET or SPECT scanner. Since patients often experience great difficulty in remaining motionless not only while being scanned on one machine, but being moved from machine to machine, it can be problematic to register and align the images obtained from the two machines. Furthermore, creating a single "fusion" image from multiple scans requires merging of images with different resolutions and fields of view.

In the context of CT scanning, a "target material" or "target substance" has a mass density greater than about 1 g/cc so as to be visible against a water or water equivalent background but having an upper mass density that is specific to the X-ray energy of the CT scanner so as not to leave artifacts. Artifacts interfere with image quality and it is therefore desirable to eliminate them in images. For example, for a scanner using 50 kVp X-rays, the upper limit of the mass density greater than about 2 g/cc would leave artifacts in the image. For scanners using up to 120 kVp X-rays, the upper limit of the mass density is about 3 to 3.5 g/cc. For MRI scanners, the "target material" or "target substance" is a paramagnetic material. For optical scanners, a "target material" or "target substance" is scintillation material along with a material to activate the scintillation material.

There exist multimodal markers which are formed of target material having wells that are fillable with radioactive solutions for one time use. These markers are inconvenient to use since they require filling with the radioactive solution by the end user immediately before use.

Although the encapsulation portion of known sealed radioactive sources may be formed of materials that show up on a CT scan, these sealed radioactive sources are not designed or intended for use in the calibration, registration or alignment of images taken on different scanners.

It would be valuable to have a source that can be repeatedly used without filling with a radioactive solution prior to use and formed in a variety of shapes and configurations suitable to an end user's requirement.

SUMMARY OF THE INVENTION

To permit the greatest utilization in a variety of scanners, including dual CT/PET scanners, and CT, MRI or optical scanners used in conjunction with PET and/or SPECT scanners, a single sealed radioactive source designed to be used as a calibration or reference source for medical imaging detectors such as gamma cameras, SPECT, CT, MRI, PET and optical scanners is provided.

Briefly, one embodiment of the invention comprises a multimodal source for imaging with at least one of a gamma camera, a positron emission tomography (PET) scanner and a single-photon-emission computed tomography (SPECT) scanner, and at least one of a computed tomography (CT) scanner, magnetic resonance imaging (MRI) scanner, and optical scanner. The multimodal source comprises radioactive material and at least one material that is a target for at least one of CT scanning, MRI scanning and optical scanning.

For CT scanning, a "target material" or "target substance" has a mass density greater than about 1 g/cc so as to be visible against a water or water equivalent background but having an upper mass density that is specific to the X-ray energy of the CT scanner so as not to leave artifacts. Artifacts interfere with image quality and it is therefore desirable to eliminate them in images. For example, for a scanner using 50 kVp X-rays, the upper limit of the mass density greater than about 2 g/cc would leave artifacts in the image. For scanners using up to 120 kVp X-rays, the upper limit of the mass density is about 3 to 3.5 g/cc. For MRI scanners, the "target material" or "target substance" is a paramagnetic material. For optical scanners, a "target material" or "target substance" is scintillation material along with a material to activate the scintillation material.

The source comprises a solid or sealed radioactive component utilizing one or more radionuclide, which can include Ag-110m, Am-241, Au-195, Ba-133, C-14, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137 and Se-75 being particularly good nuclides to provide for PET and SPECT visibility and one or more of the following: barium or iodine salts (as well as other known compounds that are targets for CT scans such as bone-equivalent density material such as alumina ceramic or high density plastic, polymers or glass) to provide a target for CT scanners; and gadolinium salts and other paramagnetic MRI imaging substances to provide MRI targets and scintillator materials to provide optical targets.

The source can have any of numerous shapes, including but not limited to a point, a ring, a line, a plane, a cylinder, a box, and anthropomorphic shapes such as heart, breast, torso, brain, or thyroid mimics. The radioactive and CT-, MRI- and/or optical target materials may be localized in certain regions of the source and/or distributed throughout the source and can be presented in a matrix of material. The radioactive and CT-, MRI- and/or optical target materials may also be incorporated into a single element, superimposed in layers or consecutive structures, or placed in separate locations.

For three-dimensional phantoms intended for medical imaging (e.g., the cylinder, box, and anthropomorphic configurations, etc.), the matrix material is preferably chosen to be at a water- or tissue-equivalent density. Other densities could be used to meet the needs of other applications.

The radionuclide can best be selected from known calibrators for the detector system with which the source is to be used, or can be selected from possible radionuclides that have radiation energies similar to radionuclides used with the detector systems to be used. These radionuclides include, but are not limited to Ag-110m, Am-241, Au-195, Ba-133, C-14, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, with Ba-133, Co-57, Ge-68, Na-22, Gd-153, Cs-137 and Se-75 being particularly good nuclides to provide for PET and SPECT visibility. The particular radionuclides to be used are preferably chosen based upon factors such as their half-life (which are typically much longer than the half lives of the radionuclides used in imaging humans and animals), their energy peak correlations with radionuclides used in imaging humans and other animals, and an absence of higher energy emissions.

The intended use of these multimodal sources is for image coregistration (e.g., when images are taken on two or more machines), quality control, resolution and contrast measurements, and qualitative or quantitative scatter and attenuation measurements for medical imaging detectors. Other uses and configurations may be possible for nonmedical and more general scientific imaging applications.

DETAILED DESCRIPTION

Figure 1:
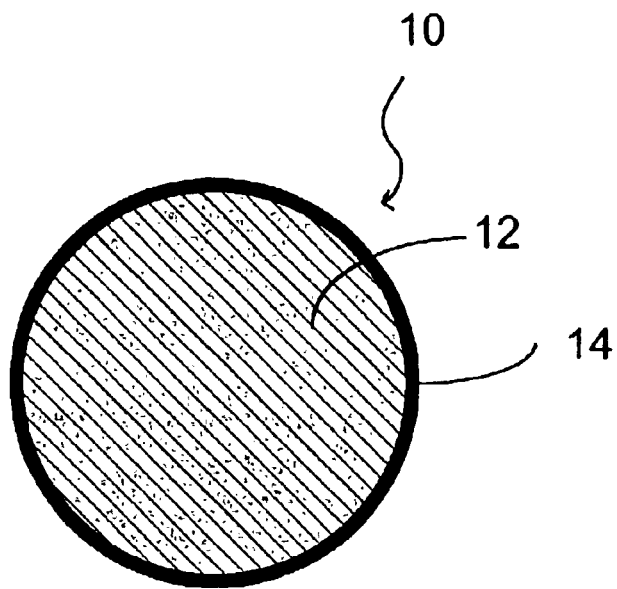
FIG. 1 is a schematic cross sectional view illustrating a first embodiment of a source of the invention comprising a point source.

The multimodal source of the invention can be provided in a wide variety of configurations. FIG. 1 shows a cross sectional first embodiment of the source 10 of the invention comprising a point source in the form of a spherical source with both radioactive and CT/MRI/optical target materials. The point source can be conveniently sized at approximately 5 mm in diameter or smaller. In this embodiment, a core 12 of the source can be formed of a matrix (such as a polymeric resin, a cement, a silicone, a ceramic, a polymer gel, etc.) with one or more radionuclides such as Ag-110m, Am-241, Au-195, Ba-133, C-14, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95, (with Ba-133, Co-57, Ge-68, Na-22, Gd-153, Cs-137 and Se-75 being particularly good nuclides) mixed in, and a coating of barium or iodine salts, bone-equivalent density material such as alumina ceramic, as well as other known compounds such as dense plastics, polymers or glass that are CT target material mixed in an outer coating layer 14 that surrounds core 12 to provide CT targets. For a source that is usable with PET or SPECT scanners and MRI scanners, the coating 14 can, for example, comprise gadolinium salts and other known MRI target materials in a matrix, such as a polymeric resin base. The ordering of materials making up of core 12 and outer layer 14 can be reversed if desired, and it is likewise possible to provide a point source with MRI and CT and optical target substances mixed together and included as a single coating 14. It is also possible to provide the CT, MRI and/or optical target substances mixed together with the radionuclide in core 12 and forego the outer coating having MRI, CT and/or optical target substances incorporated therein. If desired, additional coatings can be provided over the point source.

Figure 2:
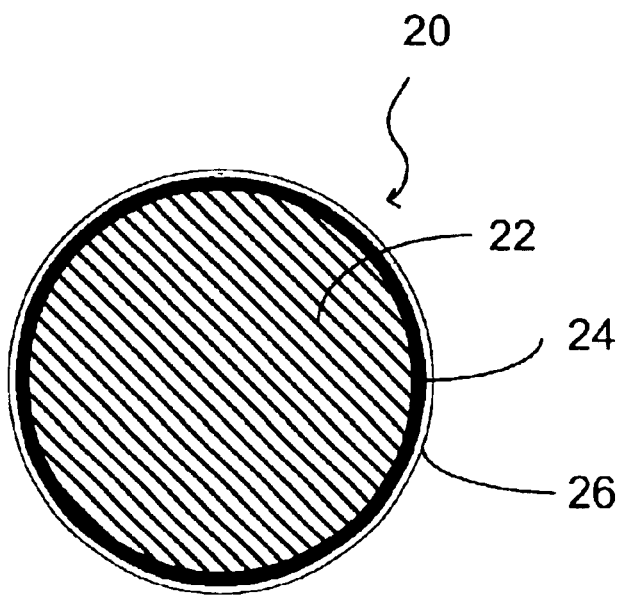
FIG. 2 is a schematic cross sectional view illustrating a single point source which incorporates MRI, CT and/or optical target substances in two separate coatings over a radioactive core.

Referring to FIG. 2, it is also possible to provide a single point source 20 which incorporates MRI, CT and/or optical target substances in either of two separate coatings 24 and 26 over a core 22.

Figure 3:
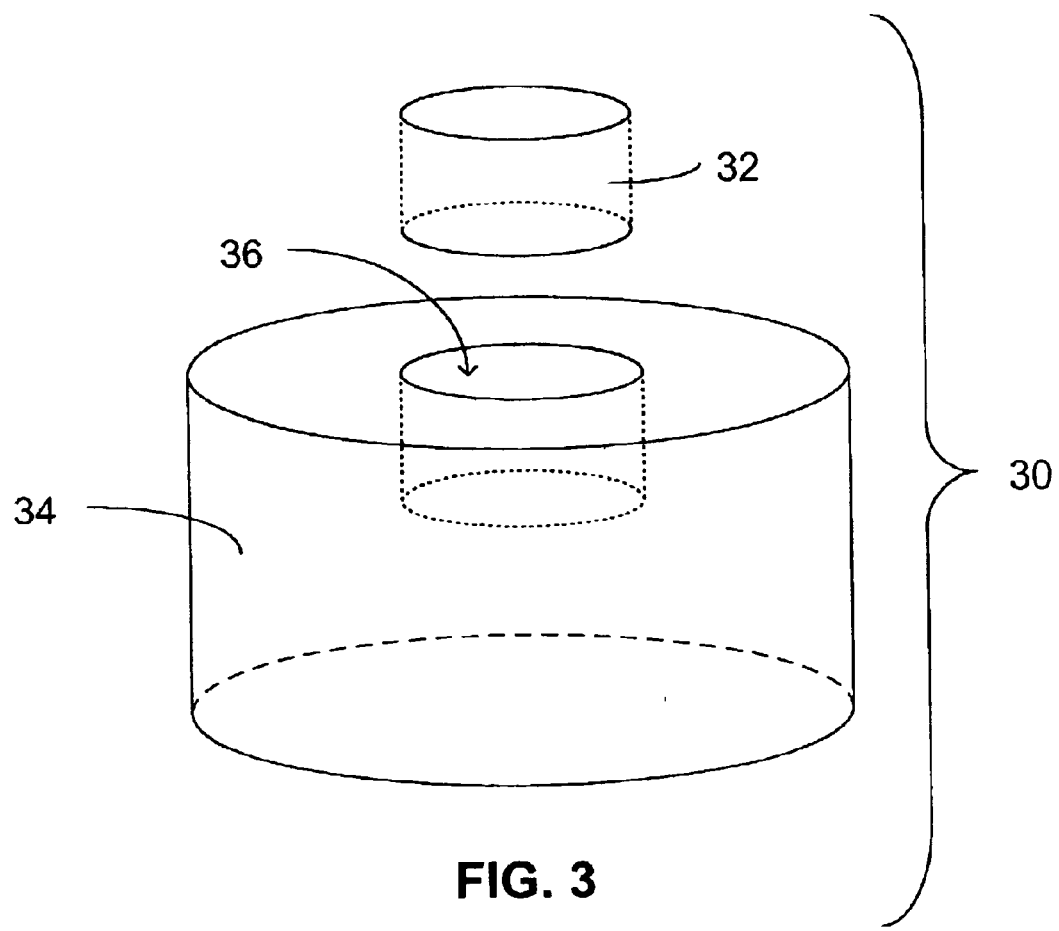
FIG. 3 is a schematic exploded perspective view of an exemplary point source with a radioactive element surrounded by a ring of CT/MRI/optical target material.
Figure 4:
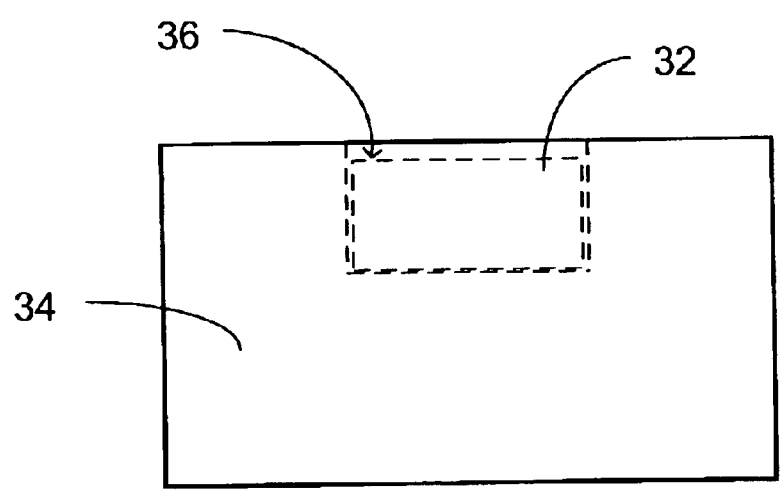
FIG. 4 is a schematic side view of the assembled source of FIG. 3.

FIGS. 3 and 4 show an exploded and a partially exposed side view, respectively, of an exemplary point source 30 with a radioactive element 32 surrounded by a ring of CT/MRI/optical target material 34. This point source can be made by providing a ring of CT/MRI/optical target material 34, sized, for example, at about 250 microns to about 3 cm with a well 36 located therein, and with a cylindrical, spherical or cubical shaped radioactive portion 32 sized with a diameter of about 100 microns to 5 mm. A glue or a polymeric resin or other material or covering such as plastic film can be deposited or used to cover over radioactive portion 32 to seal it in place to ring of CT/MRI/optical target material 34. Other dimensions and configurations can be provided.

Figure 5:
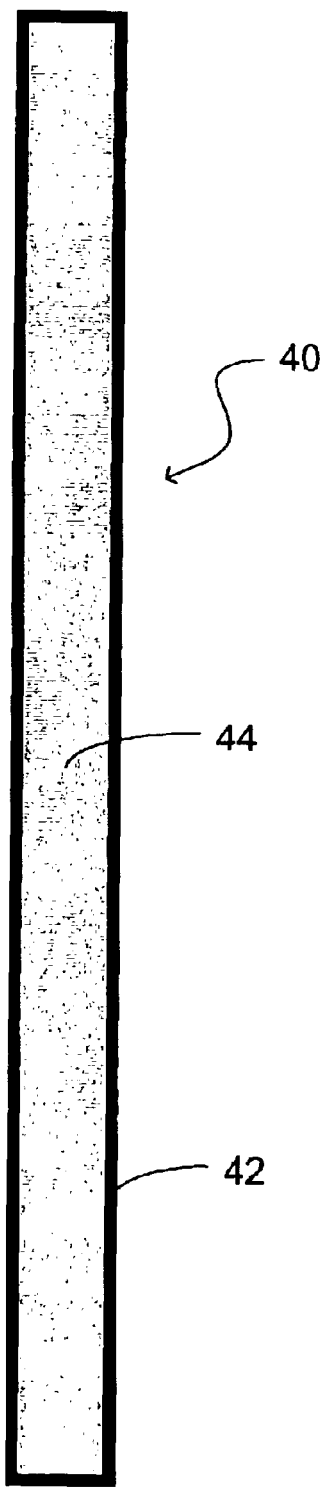
FIG. 5 is a schematic top plan view of an exemplary line source having both radioactive and CT/MRI/optical target material incorporated uniformly through an active core area of source.

FIG. 5 is a side view of an exemplary line source 40 having both radioactive and CT/MRI/optical target material incorporated uniformly through an active core area 44 of source 40. A protective outer layer 42 (such as stainless steel, a plastic tubing, etc.) envelopes active core area 44. Line source may be rigid or flexible, and, for example, can have a diameter of 100 microns to 2 cm and a length of 70 cm or smaller.

Figure 6:
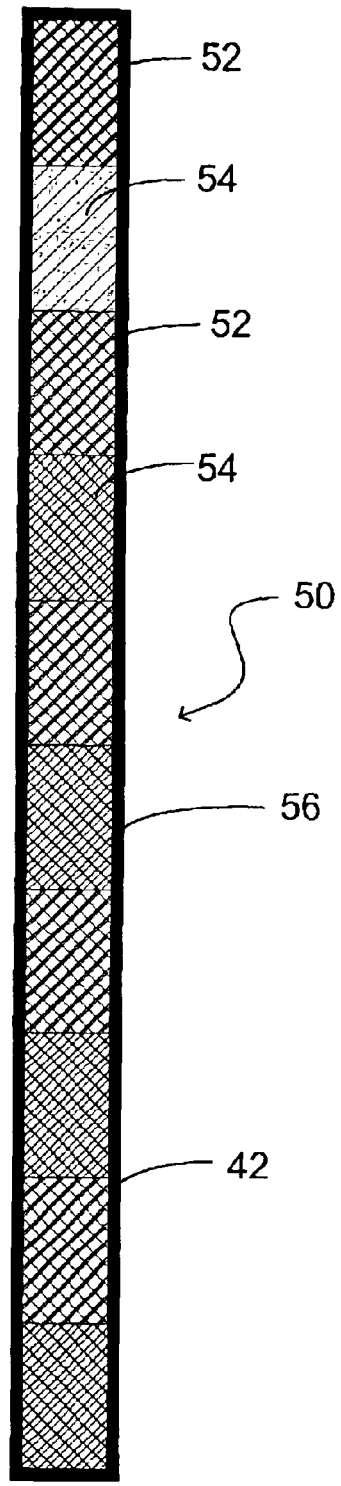
FIG. 6 is a schematic top plan view of an exemplary embodiment of a line source having alternating segments of radioactive and CT/MRI/optical target material.

FIG. 6 is a side view of an exemplary embodiment of a line source 50 having alternating segments of radioactive material 52 and CT/MRI/optical target material 54. A protective outer layer 56 (such as stainless steel, a plastic tubing, etc.) envelopes active core area comprising alternating sections 52 and 54. Line source 50 may be rigid or flexible, and, for example, can have a diameter of 100 microns to 2 cm and a length of 70 cm or smaller.

Figure 7:
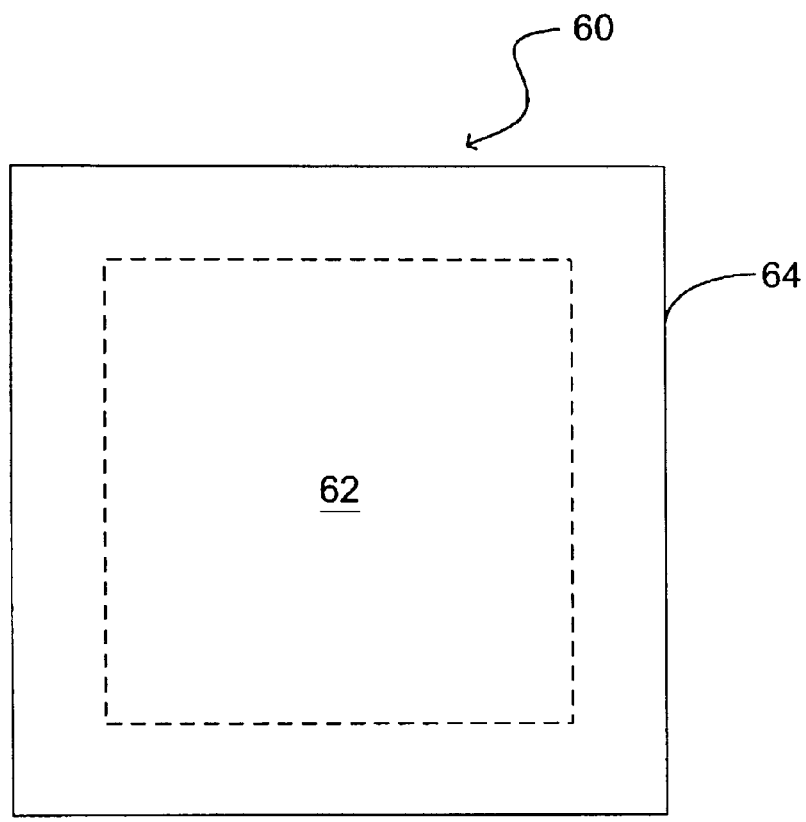
FIG. 7 is a partially exposed schematic top plan view of an exemplary embodiment of a plane source with both radioactive and CT/MRI/optical target material incorporated uniformly throughout the active area of the source surrounded by a protective envelope.

FIG. 7 is a partially exposed top plan view of an exemplary embodiment of a plane source 60 with both radioactive material and CT/MRI/optical target material incorporated uniformly throughout the active area 62 of the source surrounded by a protective envelope 64. The active area can be sized as desired, such as 75 cm×65 cm or smaller such 1 cm×2 cm. Active areas can be provided in any number of desired shapes, such as circular (not shown) or rectangular areas, with both the radioactive material and CT/MRI/optical target material being dispersed uniformly throughout the active area of the source.

Figure 8:
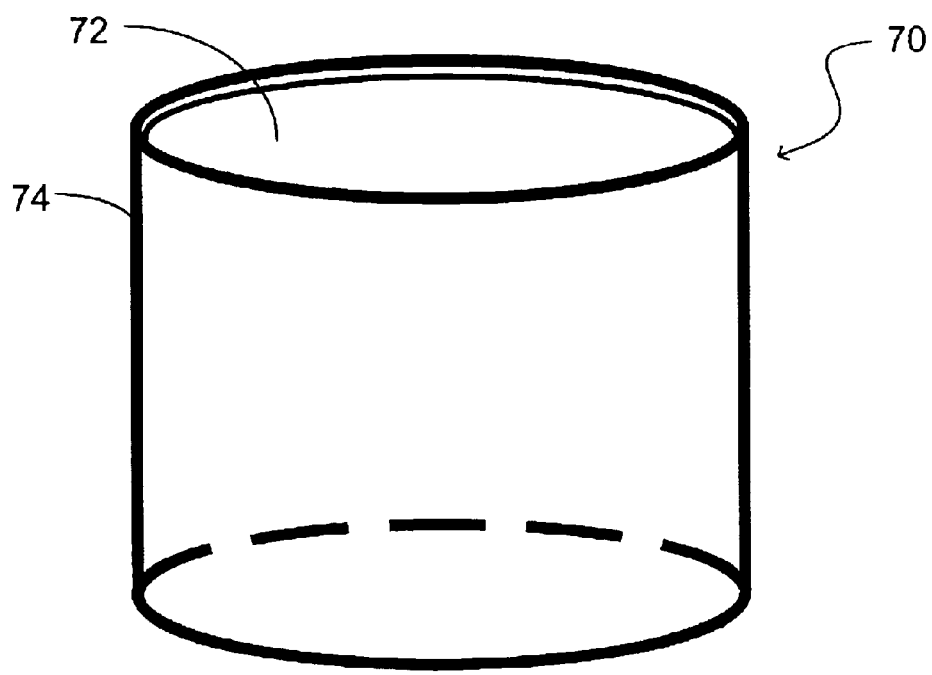
FIG. 8 is a schematic perspective side view of an exemplary embodiment of a cylinder source with radioactivity and CT/MRI/optical target material distributed throughout an active volume in the container.

FIG. 8 is a side view of an exemplary embodiment of a cylinder source 70 with radioactive and CT/MRI/optical target material distributed throughout an active volume 72 in a container 74. Cylinder source 70 can, for example, have an active dimension of around 30 cm diameter×30 cm height. Other sizes can be provided as desired.

Figure 9:
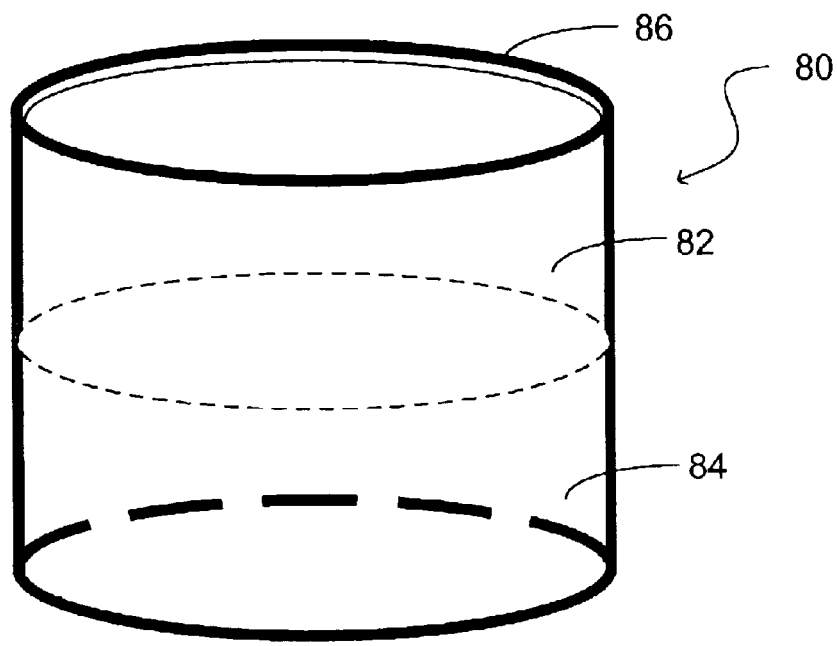
FIG. 9 is a schematic side view of an alternate embodiment of a cylinder source where radioactivity and CT/MRI/optical target material are distributed in their own discrete regions in a container.

As shown in FIG. 9, in an alternate embodiment of a cylinder source 80, radioactive material and CT/MRI/optical target material are distributed in their own discrete regions 82 and 84 within a container 86. Although not shown, the cylindrical containers of the embodiments of FIGS. 8 and 9 can be replaced with a box shaped container if desired.

Anthropomorphic shapes such as a heart, breast, torso, or thyroid mimic, with radioactivity and CT/MRI/optical target material distributed throughout the active volume or in discrete regions within the volume of the source can also be provided.

Figure 10:
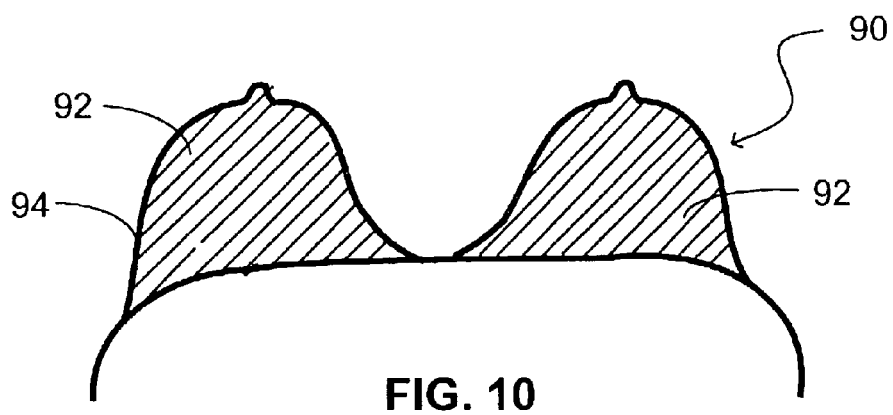
FIG. 10 is a schematic view illustrating a partially exposed side view of a first embodiment of an anthropomorphic breast phantom with radioactive and CT/MRI/optical target material distributed evenly throughout the active volumes of material.

FIG. 10 is a partially exposed side view of an anthropomorphic breast phantom 90, with radioactive and CT/MRI/optical target material distributed even throughout the active volumes of material 92 (such as polymeric resins, cements, silicones, polymer gels, ceramics, etc.), with active volumes 92 being encased with walls 94.

Figure 11:
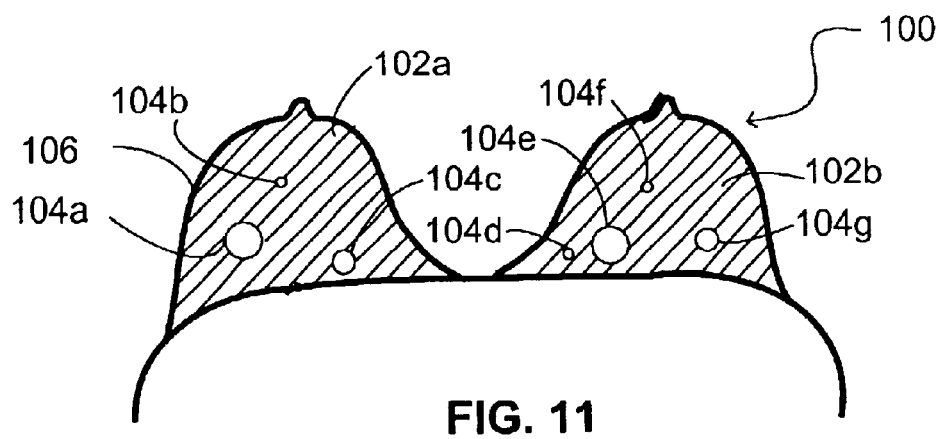
FIG. 11 is a schematic view illustrating another embodiment of a partially exposed side view of an anthropomorphic breast phantom wherein radioactive material is distributed in regions separated from the areas having CT/MRI/optical target material.

FIG. 11 is another embodiment of a partially exposed side view of an anthropomorphic breast phantom 100, wherein radioactive material is distributed in one region of the volumes 102A and 102B and CT/MRI/optical target material are distributed throughout other active areas 104a–g, with the structure being surrounded by walls 106. In this embodiment, as well as the other embodiments described above and below, the discrete regions of material 104a–g can be constructed to provide different visibility densities for a single modality and/or multiple modalities. For example, the active areas can have differing levels of radioactivity (from no level to a high level) and/or can comprise radioactive materials with increasing amounts of CT, MRI and/or optical target materials.

Figure 12:
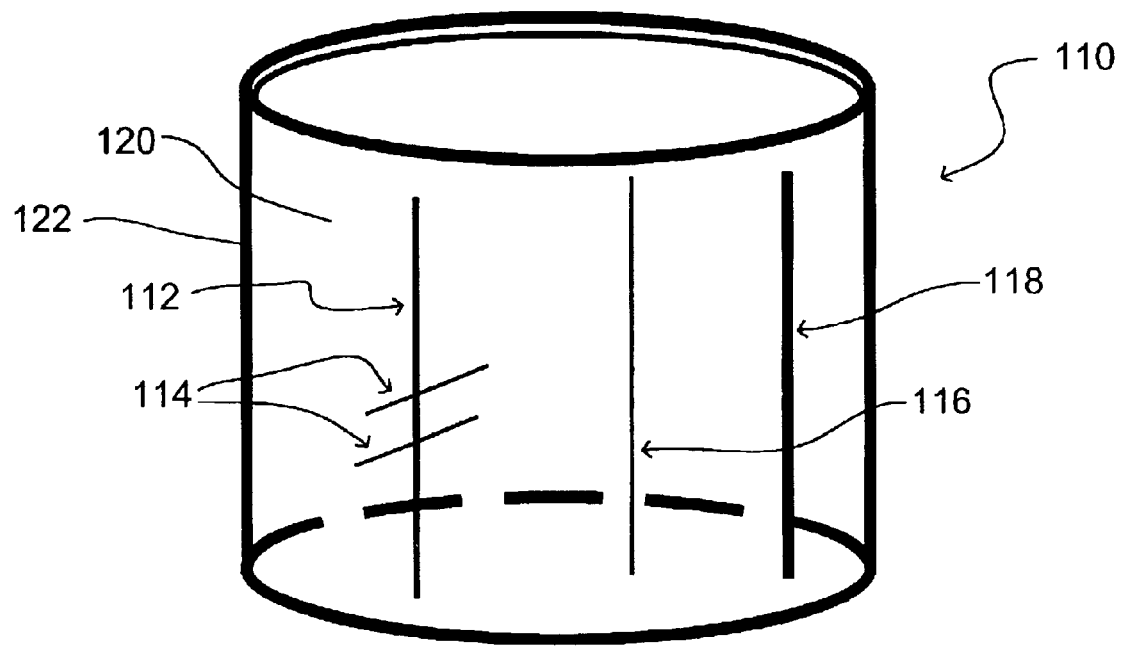
FIG. 12 is a schematic perspective view of an exemplary small animal phantom that includes objects that mimic animal bone structures.
Figure 13:
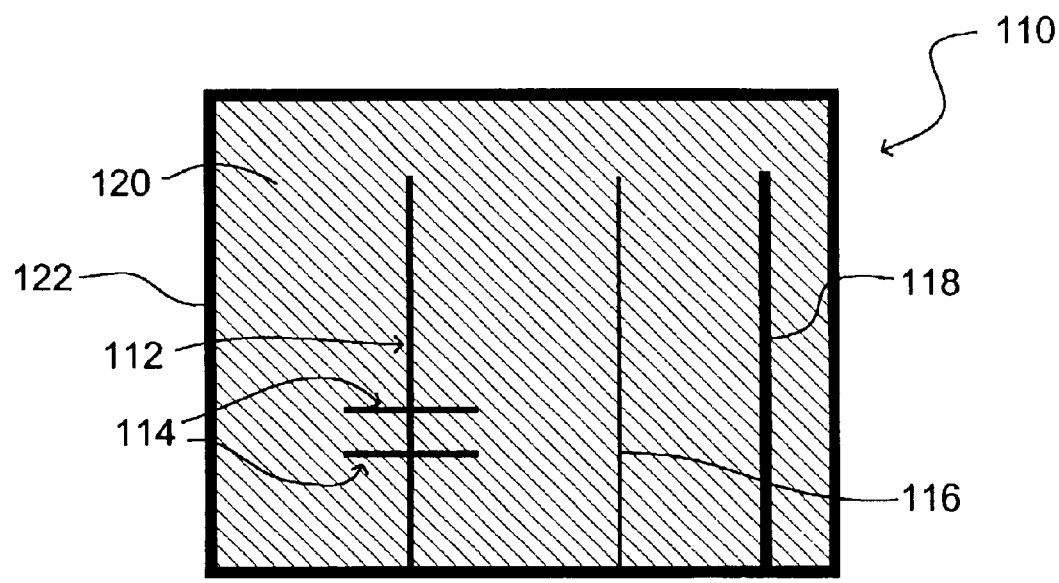
FIG. 13 is a schematic cross-sectional view of the phantom of FIG. 12.

Turning to FIGS. 12 and 13, there are shown a perspective view and a cross-sectional view, respectively, of an exemplary small animal phantom 110 that includes objects that mimic, for example, animal structures, such as a spine 112 and ribs 114, and rodlike structures 116 and 118 (e.g., of different diameter) that can be used to calibrate a scanner and/or measure the scanner's resolution. The mimicking objects are contained in a background of radioactive material 120, which in turn are contained in a container 122.

In all embodiments of the multimodal sources, the amount of the nuclide can be varied as required by the specific application. By way of example, the amount can range from about 10 nanocuries (mCi) (370 becquerels (Bq)) or less to about 10 millicuries (mCi) (370 megabecquerels (MBq)) or more. Moreover, combinations of different radionuclides can be provided in a single source. It is desirable for the material matrix to be a solid, semi-solid, or cross-linked gel type of material (such as silicones) so that the positioning of any objects in the matrix remains constant. Any of these embodiments may also include internal structures such as points, cylinders, rods, planes, etc., that provide varying levels of visibility for each modality.

As noted above, for CT scanning, a "target material" or "target substance" has a mass density greater than about 1 g/cc so as to be visible against a water or water equivalent background but having an upper mass density that is specific to the X-ray energy of the CT scanner so as not to leave artifacts. Artifacts interfere with image quality and it is therefore desirable to eliminate them in images. For example, for a scanner using 50 kVp X-rays, the upper limit of the mass density greater than about 2 g/cc would leave artifacts in the image. For scanners using up to 120 kVp X-rays, the upper limit of the mass density is about 3 to 3.5 g/cc. For MR scanners, the "target material" or "target substance" is a paramagnetic material. For optical scanners, a "target material" or "target substance" is scintillation material along with a material to activate the scintillation material.

Having thus described exemplary embodiments of the present invention, it should be understood by those skilled in the art that the above disclosures are exemplary only and that various other alternatives, adaptations and modifications may be made within the scope of the present invention. The presently disclosed embodiments are to be considered in all respects as illustrative and not restrictive. The scope of the invention being indicated by the claims, rather than the foregoing description, and all changes which come within the meaning and range of equivalency of the claims are therefore intended to be embraced therein.

What is claimed is:

1. A multimodal source for imaging with at least one of a gamma camera, a positron emission tomography (PET) scanner and a single-photon-emission computed tomography (SPECT)scanner, and at least one of a computed tomography (CT) scanner, magnetic resonance imaging (MRI) scanner and optical scanner, the multimodal source comprising:
   radioactive material; and
   at least one material that is a target material for at least one of CT scanning, MRI scanning and optical scanning, wherein the radioactive material and at least one material are permanently incorporated into a single multimodal source.

2. The multimodal source of claim 1, wherein the radioactive material is incorporated into a matrix of material.

3. The multimodal source of claim 2, wherein the matrix of material is selected from the group consisting of polymeric resins, urethanes, silicones, polymer gels, cements, and castable ceramics.

4. The multimodal source of claim 1, wherein the radioactive material is incorporated into a matrix of material, which radioactive matrix is adjacent to layers or structures containing at least one of the materials that is a target material for CT scanning, MRI scanning and optical scanning.

5. The multimodal source of claim 1, further comprising a container.

6. The multimodal source of claim 5, wherein the container is formed in the shape of a ring formed of the at least one of a material that is a target for CT, MRI and optical scans, the container having a recess into which the radioactive material is placed.

7. The multimodal source of claim 5, wherein the radioactive material and the at least one of the materials that is a target for CT, MRI and optical scanning are dispersed throughout a material located in the container.

8. The multimodal source of claim 5, wherein the radioactive material and the at least one of the materials that is a target for CT, MRI and optical scanning are contained in separate regions within the container.

9. The multimodal source of claim 1, wherein the radioactive material is at least one radionuclide selected from the group consisting of Ag-110m, Am-241, Au-195, Ba-133, C-14, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

10. The multimodal source of claim 1, wherein the radioactive material is at least one radionuclide selected from the group consisting of Ba-133, Co-57, Ge-68, Na-22, Gd-153, Cs-137, and Se-75.

11. The multimodal source of claim 1, wherein the material that is a target for CT scans is selected from the group consisting of bone-equivalent density material, ceramics, high density plastic, polymers and glass, and barium salts and iodine salts.

12. The multimodal source of claim 5, wherein the container is cylindrical in shape.

13. The multimodal source of claim 5, wherein the container has an anthropomorphic shape.

14. The multimodal source of claim 5, wherein the container has the shape selected from a flat sheet, a cube and a sphere.

15. The multimodal source of claim 1, wherein the material that is a target for CT, MRI, and/or optical scans is sized and shaped into at least one of a biological mimicking structure.

16. The multimodal source of claim 15, wherein the at least one biological mimicking structure is contained in a container in a matrix of radioactive material.

17. A multimodal source for imaging with at least one of a gamma camera, a positron emission tomography (PET) scanner and a single-photon-emission computed tomography (SPECT)scanner, and at least one of a computed tomography (CT) scanner, magnetic resonance imaging (MRI) scanner and optical scanner, the multimodal source comprising:
    radioactive material formed into a matrix of material;
    at least one material that is a target for at least one of CT scanning, and MRI scanning and optical scanning; and
    a container for containing the matrix of material and the at least one material that is a target for at least one of CT scanning, MRI scanning and optical scanning, wherein the radioactive material and at least one material are permanently incorporated into a single multimodal source.

18. The multimodal source of claim 17, wherein the matrix of material is selected from the group consisting of polymeric resins, urethanes, silicones, polymer gels, cements, and castable ceramics.

19. The multimodal source of claim 17, wherein the radioactive material and the at least one of the material that is a target for CT scanning, MRI scanning and optical scanning are dispersed throughout the matrix of material located in the container.

20. The multimodal source of claim 17, wherein the radioactive material and the at least one of the material that is a target for CT scanning, MRI scanning and optical scanning are contained in separate regions in the container.

21. The multimodal source of claim 17, wherein the radioactive material is at least one radionuclide selected from the group consisting of Ag-110m, Am-241, Au-195, Ba-133, G-14, Cd-109, Ce-139, Co-57, Co-60, Cs-137, Eu-152, Gd-151, Gd-153, Ge-68, Hg-203, Ir-192, I-125, I-129, I-131, Lu-173, Lu-177m, Mn-54, Na-22, Ra-226, Rh-101, Ru-103, Ru-106, Sb-125, Se-75, Sn-113, Sr-90, Ta-182, Te-123m, Tl-204, Th-228, Th-229, Th-230, Y-88, Zn-65, and Zr-95.

22. The multimodal source of claim 17, wherein the radioactive material is selected from the group consisting of Ba-133, Co-57, Ge-68, Na-22, Gd-153, Cs-137, and Se-75.

23. The multimodal source of claim 17, wherein the material that is a target for CT scans is selected from the group consisting of bone-equivalent density material, ceramics, high density plastic, polymers and glass, and barium salts and iodine salts.

24. The multimodal source of claim 17, wherein the material that is a target for CT, MRI and/or optical scans is sized and shaped into at least one of a biologically mimicking structure.

25. The multimodal source of claim 17, wherein the container has an anthropomorphic or biologically mimicking shape.

* * * * *